United States Patent

Ruppel et al.

[11] Patent Number: 5,821,390
[45] Date of Patent: Oct. 13, 1998

[54] CATALYTIC GAS-PHASE OXIDATION OF PROPENE TO ACROLEIN

[75] Inventors: Wilhelm Ruppel, Frankenthal; Ulrike Wegerle, Worms; Andreas Tenten, Neustadt; Ulrich Hammon, Mannheim, all of Germany

[73] Assignee: BASF Aktiengesellschaft, Ludwigshafen, Germany

[21] Appl. No.: 525,011

[22] Filed: Sep. 8, 1995

[30] Foreign Application Priority Data

Sep. 8, 1994 [DE] Germany ............. 44 31 957.6

[51] Int. Cl.⁶ ................................. C07C 47/22
[52] U.S. Cl. ............................................. 568/470
[58] Field of Search ................................. 568/470

[56] References Cited

U.S. PATENT DOCUMENTS

| | | |
|---|---|---|
| 3,566,961 | 3/1971 | Lorenz et al. . |
| 3,649,930 | 3/1972 | Le Floch . |
| 3,825,600 | 7/1974 | Ohara et al. . |
| 3,865,555 | 2/1975 | Elebracht et al. . |
| 3,871,445 | 3/1975 | Wanka et al. . |
| 3,901,659 | 8/1975 | Joklik et al. . |
| 4,203,906 | 5/1980 | Takada et al. . |
| 4,256,783 | 3/1981 | Takada et al. . |
| 4,298,763 | 11/1981 | Engelbach et al. . |
| 4,339,355 | 7/1982 | Decker et al. . |
| 4,365,087 | 12/1982 | Kadowaki et al. . |
| 4,873,368 | 10/1989 | Kadowaki et al. . |
| 4,885,734 | 12/1989 | Yuzo . |
| 5,144,091 | 9/1992 | Martan et al. . |
| 5,198,578 | 3/1993 | Etzkorn et al. . |
| 5,364,825 | 11/1994 | Neumann et al. . |

FOREIGN PATENT DOCUMENTS

| | | |
|---|---|---|
| 0 253 409 | 11/1991 | European Pat. Off. . |
| 0 468 290 | 3/1994 | European Pat. Off. . |
| 2 308 609 | 11/1976 | France . |
| 2 655 876 | 6/1991 | France . |
| 1 039 040 | 3/1959 | Germany . |
| 16 01 162 | 10/1970 | Germany . |
| 16 75 501 | 6/1972 | Germany . |
| 2 201 528 | 11/1972 | Germany . |
| 2 310 517 | 9/1973 | Germany . |
| 2 231 557 | 1/1974 | Germany . |
| 25 13 405 | 10/1976 | Germany . |
| 28 30 765 | 1/1980 | Germany . |
| 30 02 829 | 7/1980 | Germany . |
| 29 09 597 | 9/1980 | Germany . |
| 30 42 468 | 6/1981 | Germany . |
| 40 23 239 | 1/1992 | Germany . |
| 42 20 859 | 1/1994 | Germany . |
| 843663 | 8/1960 | United Kingdom . |
| 1 252 347 | 11/1971 | United Kingdom . |
| WO 90/06807 | 6/1990 | WIPO . |

*Primary Examiner*—C. Warren Ivy
*Assistant Examiner*—Jean F. Vollano
*Attorney, Agent, or Firm*—Oblon, Spivak, McClelland, Maier & Neustadt, P.C.

[57] ABSTRACT

A gas-phase mixture of propene and oxygen is catalytically oxidized by passing a reactant gas mixture comprising propene and oxygen through a plurality of catalyst containing contact tubes in a fixed bed reactor and simultaneously passing only one heat-exchange medium at elevated temperature over the exterior surfaces of the contact tubes in a longitudinal flow pattern which is cocurrent with the direction of flow of the reactants through said tube; simultaneously superposing a transverse flow on said longitudinal flow of heat exchange medium by means of an arrangement of successive baffles along the contact tubes which leave passage cross-sections free, thereby resulting in a meandrous flow of the heat-exchange medium through the reactor and setting the flow rate of said heat-exchange medium so that its temperature between the point of entry of the medium into the reactor and its point of exit increases by 2° to 10° C.; and obtaining product acrolein at a selectivity ≧85 mol % from the reactor at a single pass propene conversion ≧90 mol %.

16 Claims, 1 Drawing Sheet

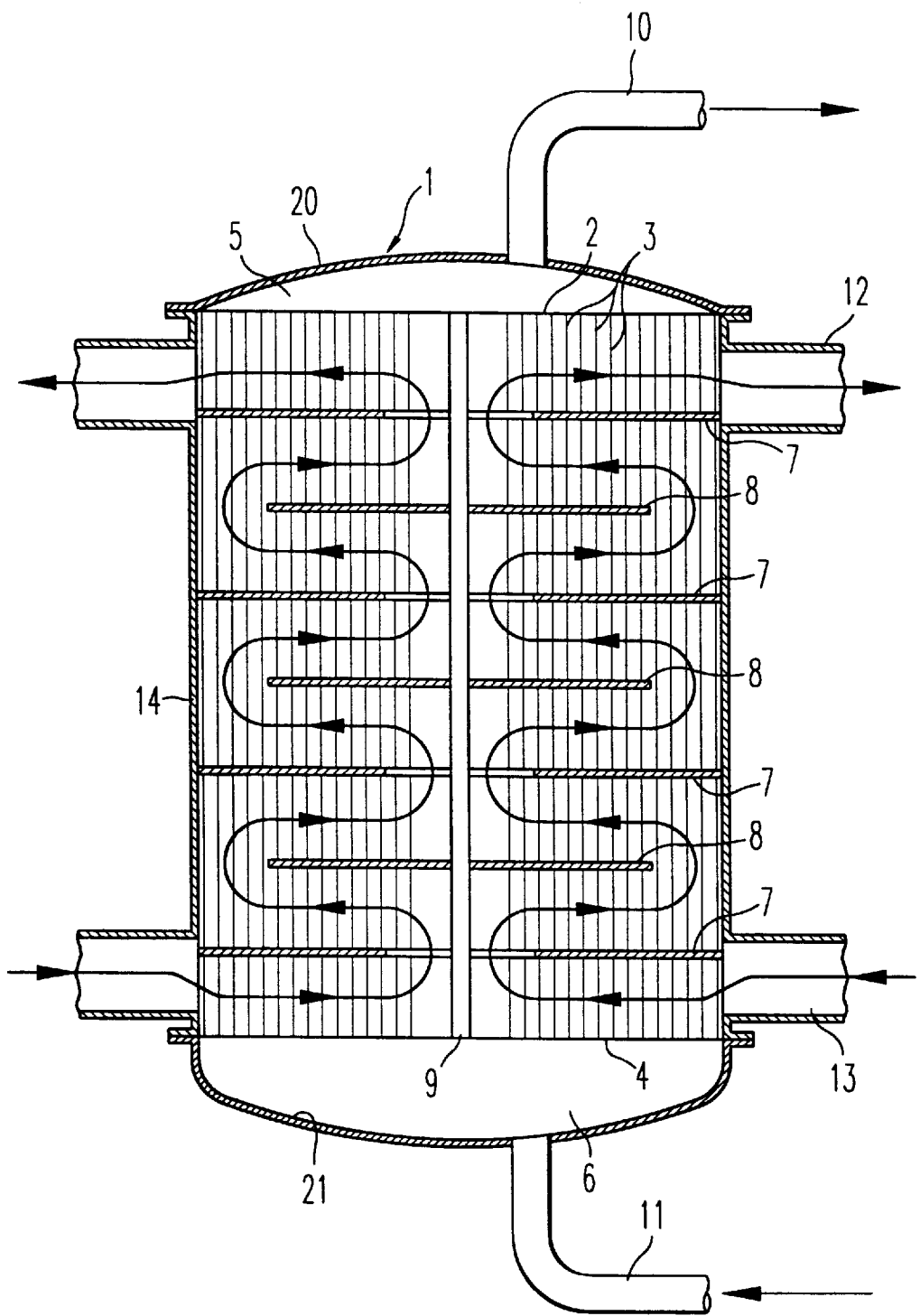

CATALYTIC GAS-PHASE OXIDATION OF PROPENE TO ACROLEIN

BACKGROUND OF THE INVENTION

1. Field Of The Invention

The present invention relates to a novel process for the catalytic gas-phase oxidation of propene to acrolein in a multiple contact tube fixed-bed reactor through whose space surrounding the contact tubes only one heat-exchange medium circuit is passed, at elevated temperature on catalytically active multimetal oxides with a propene conversion for a single pass of $\geq 90$ mol % and an acrolein formation selectivity of $\geq 85$ mol %.

2. Description Of The Background

The catalytic gas-phase oxidation of propene to acrolein is known in general terms and is particularly important as a first oxidation step in the preparation of acrylic acid by two-step catalytic gas-phase oxidation of propene in two successive reaction steps (cf., for example, DE-A 30 02 829). Acrylic acid is an important monomer which is used as such or in the form of its alkyl ester for the preparation of polymers which are suitable, for example, as adhesives.

The gas-phase oxidation of propene to acrolein is highly exothermic; for this reason, as a consequence of the wide range of possible parallel or subsequent reactions, it is necessary to control the variations in reaction temperature to a certain extent in order to give highly selective conversion of propene into acrolein and to enable the gas-phase oxidation to be carried out at all in a controllable manner.

A widely used method of controlling the heat of reaction being liberated comprises diluting the reactants oxygen and acrolein with inert gases, such as $N_2$, carbon oxides, such as $CO_2$ and CO, hydrocarbons, recycled reaction offgases and/or steam, it being particularly advantageous to use dilution gases having very high molar heat capacities (cf. EP-B 253 409).

Another generally used method of controlling the reaction temperature comprises carrying out the catalytic gas-phase oxidation of propene to acrolein in a multiple contact tube fixed-bed reactor. Such reactors correspond in design to shell-and-tube heat exchangers, ie. they usually comprise a generally cylindrical container in which a multiplicity of tubes (a tube bundle) corresponding to the cooling tubes of a shell-and-tube heat exchanger is accommodated, usually in a vertical arrangement. These contact tubes, each of which contains a fixed-bed arrangement of the appropriate catalytically active multimetal oxide, are installed with their ends in tubesheets in a sealing manner, and each runs into a bonnet, which is connected to the container at the upper or lower end. The reaction-gas mixture flowing through the contact tubes is fed in and removed via these bonnets, so that each contact tube corresponds to an extended reaction unit zone.

Furthermore, heat-exchange media are passed through the space surrounding the contact tubes in order to control the process heat. After leaving the container, the heat-exchange media, are restored to their original temperature, for example in external heat exchangers, before re-entering the reaction container (cf., for example, DE-A 30 242 468).

If heat-exchange medium enters the reactor at various (a plurality of) points along the contact tubes, we will refer here to the use of a plurality of heat-exchange medium circuits. If the heat-exchange medium enters only at one point, we will refer here to a single heat-exchange medium circuit, even if this circuit is not operated by means of one pump, but instead, for reasons of expediency, by means of a plurality of pumps.

The contact tubes are usually made of ferritic steel and typically have a wall thickness of from 1 to 3 mm. Their internal diameter is generally from 20 to 30 mm. The tube length normally extends to a few meters (a typical contact tube length is in the range from 2 to 4 m). For technical reasons, a number of contact tubes accommodated in the container is expediently at least 5000, preferably at least 10,000. The number of contact tubes accommodated in the reaction container is frequently from 15,000 to 30,000. Tube-bundle reactors with more than 40,000 contact tubes are something of an exception. Within the container, the contact tubes are normally homogeneously distributed, distribution expediently being selected so that the distance between the central internal axes of contact tubes lying closest to one another (the contact tube spacing) is from 35 to 45 mm (cf., for example, EP-B 468 290).

Suitable heat-exchange media are, in particular, fluid temperature-controlled media. Particularly favorable is the use of melts of salts such as potassium nitrate, potassium nitrite, sodium nitrite and/or sodium nitrate, or of low-melting metals, such as sodium, mercury and alloys of various metals.

DE-C 2 513 405 discloses controlling the variations in reaction temperature in the catalytic gas-phase oxidation of propene to acrolein in a multiple contact tube fixed-bed reactor on catalytically active oxides for propene conversions for a single pass of at least 90 mol % by circulating a salt melt at 330° C. through the space surrounding the contact tubes and feeding in the reaction-gas mixture after preheating to this temperature.

DE-A 30 42 468 and DE-A 30 02 829 recommend passing the heat-exchange medium and reaction-gas mixture in cocurrent through the multiple contact tube fixed-bed reactor in order to smooth out the temperature distribution within the catalyst beds. In order that a high proportion of the contact tubes participate equally in the reaction proceedings, the prior art (for example German Patent 16 01 162) recommends aiming at a very homogeneous temperature of the heat-exchange medium in a horizontal section through the reactor (perpendicular to the reactor axis). The prior art furthermore recommends passing the heat-exchange medium through the reactor rapidly in order to dissipate the liberated heat of reaction as effectively as possible. It is recommended that the heat-exchange medium is circulated in such a way that the temperature difference between the heat-exchange medium employed between the point of entry and exit from the reactor is negligible.

A general problem in the catalytic gas-phase oxidation of propene to acrolein in multiple contact tube fixed-bed reactors is that the reaction temperature in the flow direction along a contact tube passes through a maximum, known as a hot spot. This shortens the life of the catalyst in this contact tube section and also impairs the selectivity of acrolein formation.

Various countermeasures against these disadvantages have already been recommended in the prior art. One proposal comprises reducing the diameter of the contact tubes and thus increasing the heat dissipation per unit volume of the catalyst. However, this method has the disadvantage that it inevitably increases the number of catalyst-filled contact tubes required for a certain production output, which increases both production costs of the reactor and the time necessary for filling and emptying the contact tubes with catalyst.

In another proposed process, it is attempted to suppress the formation of hot spots by varying the volume-specific activity of the catalytic charge along the contact tubes. However, this procedure inevitably requires either the use of at least two catalysts of different activity or the additional use of inert material. Furthermore, this procedure inevitably complicates filling of the contact tubes (an overview of the various countermeasures proposed is given, for example, in German Patent 28 30 765). Another obvious way of reducing the formation of hot spots comprises reducing the propene flow rate into the reactor. However, this measure also reduces the space-time yield of the target product.

DE-A 40 23 239 recommends carrying out the catalytic gas-phase oxidation of propene to acrolein in such a way that the reaction temperature in the flow direction along the contact tubes is from 360° to 420° C. from the point of entry of the reaction gases containing the reactants into the contact tubes as far as the point where a propene conversion of from 30 to 70 mol % is achieved, is subsequently from 360 ° to 300° C. as far as the point where a propene conversion of from 80 to 90 mol % is achieved, and is then kept at from 330° to 390° C. until the reaction-gas mixture leaves the contact tubes. However, this procedure has the disadvantage that the establishment of such a temperature profile requires the use of more than one heat-exchange medium circuit.

In addition to the possibility of simply conveying the heat-exchange medium essentially directly longitudinally to the contact tubes, DE-A 22 01 528 also comprises the possibility, for exothermic, catalytic, multiple contact tube fixed-bed oxidations, of accomplishing this longitudinal conveying merely considered over the reaction container as a whole and superposing a transverse flow on this longitudinal flow within the reaction container by means of an arrangement of successive baffles along the contact tubes which leaves passage cross sections free, so as to give a meandrous flow pattern of the heat-exchange medium in longitudinal section through the tube bundle. This proposal is also included in German Patent 28 30 765, DE-A 2 231 557 and DE-A 2 310 517.

Trans I Chem. E, Vol. 71, Part B, August 1993, p. 208 to 214, discloses that complex indirect interactions take place between the heat outputs of the individual contact tubes in exothermic catalytic multiple contact tube fixed-bed oxidations, causing the position of the hot spot and the magnitude thereof generally to differ in the individual contact tubes and being virtually impossible to predict.

SUMMARY OF THE INVENTION

In view of this prior art, it is an object of the present invention to provide a novel process for the catalytic gas-phase oxidation of propene to acrolein in a multiple contact tube fixed-bed reactor through whose space surrounding the contact tubes only one heat-exchange medium circuit is passed, at elevated temperature on catalytically active multimetal oxides, which process is able to give a predetermined propene conversion ($\geq 90$ mol % for a single pass) and a predetermined acrolein formation selectivity ($\geq 85$ mol %) (ie. a predetermined space-time yield of acrolein) for a given propene-containing reaction mixture at a given catalyst charge and predetermined propene flow rate, in a very simple and favorable manner with formation of reduced hot-spot temperatures.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

the FIGURE shows a reactor embodiment of the invention in which a reactant gas mixture and heat exchange medium flow concurrently therethrough.

DEATAILED DESCRIPTION OF THE PREFFERRED EMBODIMENTS

We have found that this object is achieved by a process for the catalytic gas-phase oxidation of propene to acrolein in a multiple contact tube fixed-bed reactor through whose space surrounding the contact tubes only one heat-exchange medium circuit is passed, at elevated temperature on catalytically active multimetal oxides with a propene conversion for a single pass of $\geq 90$ mol % and an acrolein formation selectivity of $\geq 85$ mol %, which comprises firstly passing the heat-exchange medium through the multiple contact tube fixed-bed reactor longitudinally, considered over the reaction container as a whole, to the contact tubes in cocurrent to the reaction-gas mixture and secondly superposing a transverse flow within the reaction container by means of an arrangement of successive baffles along the contact tubes which leaves passage cross sections free, so as to give a meandrous flow of the heat-exchange medium, seen in longitudinal section through the tube bundle, with the proviso that the flow rate of the circulated heat-exchange medium is set so that its temperature rises by from 2° to 10° C., preferably from 3° to 6° C., between the point of entry into the reactor and the point of exit out of the reactor.

German Patent 1 601 162, in column 2, advises against such an embodiment since it makes it impossible to achieve sufficiently uniform tube temperatures over the reactor cross section.

The temperature of the heat-exchange medium on entry into the reactor is selected in a manner known per se so that, for a given catalyst charge and a predetermined propene flow rate, the reaction temperature profile necessary in order to achieve the required propene conversion and the required acrolein selectivity becomes established. The reaction temperatures in such a profile are usually from 300° to 450° C. when the multimetal oxide catalysts comprising molybdenum, bismuth and iron in oxidic form which are known for this purpose are used. Correspondingly, preferred entry temperatures of the heat-exchange medium are from 280° to 380° C. Such suitable multimetal oxide catalysts are mentioned, for example, in U.S. Pat. Nos. 3,825,600,3,649, 930 and U.S. Pat. No. 4,339,355. Furthermore, the multimetal oxide compositions of DE-A 42 20 859 are particularly suitable.

A multiplicity of suitable multimetal oxide catalysts, can be summarized under the formula I $$Mo_{12} Bi_a Fe_b X^1_c X^2_d X^3_e X^4_f O_n \qquad (I),$$

where $X^1$ is nickel and/or cobalt, $X^2$ is thallium, an alkali metal and/or an alkaline earth metal, $X^3$ is phosphorus, arsenic, boron, antimony, tin, cerium, lead and/or tungsten, $X^4$ is silicon, aluminum, titanium and/or zirconium, a is from 0.5 to 5, b is from 0.01 to 3, c is from 3 to 10, d is from 0.02 to 2, e is from 0 to 5, f is from 0 to 10 and n is a number determined by the valency and frequency of the elements other than oxygen.

They are obtainable in a manner known per se (see, for example, the earlier application DE-A 40 23 239) and are usually shaped in solid form to give spheres, rings or cylinders or alternatively are employed in the form of coated catalysts, ie. preshaped, inert support elements coated with the active material. However, they can of course also be used in powder form as catalysts.

The oxidant used is oxygen. If $N_2$ is chosen as inert diluent gas, the use of air as oxygen source has proven particularly advantageous.

In general, a propene:oxygen:inert gases (including steam) ratio by volume (standard liters) of from 1:(1.0 to 3.0):(5 to 25) preferably from (1:(1.7 to 2.3):(10 to 15), is used. The reaction pressure is usually in the range from 1 to 3 bar, and the overall space velocity is preferably from 1500 to 2500 l(s.t.p.)/l/h.

The novel process does not give pure acrolein, but a mixture from whose secondary components acrolein can be separated off in a manner known per se. If the acrolein is used to prepare acrylic acid by two-step catalytic gas-phase oxidation of the propene, the acrolein-containing reaction gases are generally transferred into the second oxidation step without removal of the secondary component.

With respect to the material, size, number and spacing of the contact tubes and possible heat-exchange media, the comments made above in the assessment of the prior art apply to the novel process. The preferred heat-exchange medium according to the invention is a salt melt consisting of 60% by weight of potassium nitrate ($KNO_3$) and 40% by weight of sodium nitrite ($NaNO_2$).

The transverse flow necessary according to the invention can be generated, for example, as shown in the FIGURE, by using an arrangement of alternating baffles 7 and 8 which leaves a passage cross section free alternately on the opposite sides of the reaction container (cf. for example, DE-B 10 39 040). However, with increasing design capacity of the reactor 1, in which, due to the large number of contact tubes 2, the ratio between the diameter and length of the reaction container is also correspondingly large, preference is given to an arrangement of baffles 7 and 8 which leaves a passage cross section free alternately in the center and at the outer periphery (additional feature a) (such baffles 8 can be attached, for example, to a rod 9 installed vertically in the center of the reactor, while baffles 7, each open in the center, are attached to the interior wall 14 of the reactor 1), so that the heat-exchange medium is passed successively from the outside inward and from the inside outward. It is advantageous to use tube bundles arranged in an essentially annular manner (where each contact tube advantageously has essentially six equidistant neighbors) with a free central space, where the diameter of the free central space is from about 10 to 30% of the reactor internal diameter (additional feature b). The distance between the outermost contact tubes and the reactor wall is normally a few centimeters. Furthermore, the contact tubes 2 are preferably not attached to the baffles in a sealing manner. Instead, gaps are advantageously left between the contact tubes and the baffles 7 and 8 (gap width generally <1 mm), so that the transverse flow rate of the heat-exchange medium is highly constant within a zone located between two successive baffles (addtional feature c). In combination with different separations of the baffles, it can further-more advantageously be achieved that the temperature differences (if possible $\leq 3°$ C.) and the pressure drops in a horizontal section within a zone are restricted (additional feature d). Furthermore, it has proven favorable in accordance with the invention if the entry and exit of the heat-exchange medium take place via ring pipelines 12 and 13 which are attached to the two ends of the reaction container and have windows distributed over the entire periphery thereof, the window openings being designed in such a way that the same amount of heat-exchange medium passes through each window per time unit (additional feature e), ensuring highly uniform radial supply and removal of the heat-exchange medium (cf. DE-A 16 01 162).

A reactant gas mixture comprising propene and oxygen enters lower bonnet 6 through line 11 and flows through the catalyst containing contact tubes 2 in cocurrent flow with the heat-exchange medium. Gaseous reaction products are collected in upper bonnet 5 and pass from the reactor through exit line 10. Bonnets 5 and 6 are formed by upper and lower tubesheets 3 and 4 and end caps 20 and 21 respectively.

It is also advantageous in accordance with the invention if a part-amount of the heat-exchange medium, preferably from 30 to 70%, particularly preferably from 40 to 60%, of the total amount of heat-exchange medium fed in is removed from the reactor (for example via a further ring pipeline for removal) at a propene conversion of from 20 to 50 mol %, preferably from 20 to 40 mol % (additional feature f). Furthermore, the reaction-gas mixture is preferably fed to the catalyst charge after prewarming to the heat-exchange medium entry temperature (additional feature g). This can be achieved in a simple manner by passing it through a bed of inert material at the appropriate temperature.

In process variants which are particularly advantageous according to the invention, as many as possible of additional features a to g are incorporated simultaneously. Particular preference is given to simultaneous incorporation of all additional features a to g. We assume that, in particular in the last-mentioned procedure, a temperature profile is achieved in the contact tube wall along an individual contact tube where the temperature of the contact tube wall is essentially constant to a propene conversion of from 20 to 50 mol % and subsequently increases by from 2° to 10° C. by the end of the tube. We furthermore assume that in this procedure, essentially uniform wall temperatures of the contact tubes also exist over the reactor cross section in the above conversion range.

Quite generally, it is attempted to restrict the number of baffles used. For technical reasons, this number is expediently from 3 to 9. A reactor type which is suitable for carrying out the particularly advantageous novel process variant is shown by FIG. 1 of DE-B 22 01 528.

It is of course possible to combine the novel procedure for reducing the hot-spot temperature for a predetermined space-time yield with the process proposals mentioned in the description of the prior art.

The novel process proves particularly suitable when the inert diluent gas in the charging-gas mixture is one which essentially comprises, preferably consists of, combustible gases, as described in the patent application filed in Germany under the file reference 19508531.0. This applies in particular when the charging-gas mixture simultaneously has an increased content by volume of $O_2$ and propylene ("rich procedure"). Inert diluent gases which are preferred in this connection are methane, ethane, propane, butane, pentane and mixtures thereof (cf. in this respect the patent applications filed in Germany under the file references 19508532.9 and 19508558.2).

In this specification, conversion U and selectivity S are defined as follows:

$$U(\text{mol }\%) = \frac{\text{Number of moles of propene reacted}}{\text{Number of moles of propene employed}} \cdot 100$$

$$S(\text{mol }\%) = \frac{\text{Number of moles of propene converted into acrolein}}{\text{Number of moles of propene reacted in total}} \cdot 100$$

for a single pass.

EXAMPLES

The data presented in the illustrative examples that follow are derived from arithmetic simulation, not actual experiment.

A. Process of the catalytic gas-phase oxidation of propene to acrolein in a multiple contact tube fixed-bed reactor in which the heat-exchange medium is passed essentially directly longitudinally to the contact tubes (comparative examples).

I. Description of the general process conditions
  Heat-exchange medium: salt melt, consisting of 50% by weight of potassium nitrate and 50% by weight of sodium nitrite;
  Contact tube material: ferritic steel;
  Dimensions of the contact tube:
    length 3200 mm;
    internal diameter: 25 mm;
    external diameter: 30 mm (wall thickness: 2.5 mm).
  Number of contact tubes in tube bundle: 15,700;
  Reactor:
    Cylindrical container having an internal diameter of 5000 mm;
    Homogeneous distribution of the contact tubes over the entire cross section with a contact tube spacing of 38 mm.
  The contact tubes are installed with their ends in 100 mm thick contact tubesheets in a sealing manner and each runs with their openings into a bonnet connected to the container at the upper or lower end.
  Feed of heat-exchange medium to the tube bundle:
  Via a ring channel around the reactor container (reactor shell). Flow in the radial direction to the tube bundle via windows over the periphery of the reactor shell.
  Separating plates which have a thickness of 10 mm and extend over the entire cross section are installed 25 mm below the upper tubesheet and 25 mm above the lower tubesheet. There are gaps allowing passage between the separating plates and the contact tubes.
  Salt melt enters the tube bundle between the lower tubesheet and the lower separating plate and distributes itself over the reactor cross section via the gaps and then rises upward parallel to the contact tubes. On reaching the upper separating plate, the salt melt flows through the gaps between the separating plate and the contact tubes and then flows into the space between the upper separating plate and the upper tubesheet radially to the outer circle of tubes and collects, via window passages, in an upper ring channel around the reactor shell and, after cooling to the original entry temperature, is pumped back into the lower ring channel. The choice of gap widths is made in accordance with German Patent 16 01 162 and DE-B 16 75 501 so that the same hydraulic resistance arises for all stream threads from the lower to the upper ring channel.

Contact tube charge:
    Coated catalyst as described in Example 1c), 1, of DE-A 29 09 597.
  Structure of the charge (from bottom to top):
    500 m bed of naked catalyst supports,
    1000 mm coated catalyst containing 37% by weight of active material,
    1700 mm coated catalyst containing 42% by weight of active material.
  Flow rate of the reaction-gas mixture:
    40,960 m$^3$(s.t.p.)/h.
  Composition of the reaction-gas mixture:
    5.4% by vol. of propene,
    10.5% by vol. of oxygen,
    1.7% by vol. of $CO_x$, i.e. CO and $CO_2$
    80.8% by vol. of $N_2$,
    1.6% by vol. of $H_2O$.
  Predetermined conversion data:
    U=95 mol %, S=90 mol %.
  Space-time yield: 202 kg of acrolein/m$^3$h.
II. Results
  The above data is achieved under the following conditions:

| Conditions | Entry temperature of the salt melt | | Exit temperature of the salt melt | Hot-spot temperature | Pump capacity (m$^3$/h) | Flow of salt melt relative to the reaction mixture |
|---|---|---|---|---|---|---|
| a) | 329° C., | Δ = 2° C., | 331° C. | 433° C. | 3,800 | Countercurrent |
| b) | 334° C., | Δ = 1° C., | 335° C. | 417° C. | 7,600 | Cocurrent |
| c) | 330° C., | Δ = 9° C., | 332° C. | 422° C. | 3,800 | Cocurrent |
| d) | 321° C., | Δ = 5° C., | 326° C. | 426° C. | 1,600 | Cocurrent |

The hot-spot temperature is determined on 5 contact tubes which are selected radially in the tube bundle to be equidistant, from the outermost to the innermost. The temperature data given show the maximum hot-spot value.
  Countercurrent flow of salt melt and reaction-gas mixture clearly cause the worst hot-spot temperatures.
  For cocurrent flow, the hot-spot conditions improve with increasing pump capacity, ie. reducing temperature difference between entry and exit temperature of the salt melt.
  Under conditions d), stable, continuous long-term operation of the reactor is no longer possible.

B) Process for the catalytic gas-phase oxidation of propene to acrolein in a multiple contact tube fixed-bed reactor in which the heat-exchange medium is passed in a meandrous manner in longitudinal section through the contact tube bundle.

I. Description of the general process conditions
  Heat-exchange material: as for A I;
  Material and dimensions of the contact tubes: as for A I;
  Number of contact tubes in the tube bundle: 25,500;
  Reactor:
    Cylindrical container having a diameter of 6800 mm. Tube bundle in an annular arrangement with a free central space.
    Diameter of the central free space: 1000 mm.
    Distance of the outermost contact tubes from the container wall: 150 mm.
    Homogeneous contact tube distribution in the tube bundle (6 equidistant and adjacent tubes per contact tube), contact tube spacing: 38 mm.

The contact tubes are installed with their ends in 125 mm thick contact tubesheets in a sealing manner and each runs with its opening into a bonnet connected to the container at the upper or lower end.

Feed of the heat-exchange medium to the tube bundle: The tube bundle is divided into four longitudinal sections (zones) of equal length (in each case 730 mm) by three baffles (each 10 mm thick) installed successively along the tube bundle between the contact tubesheets.

The lowermost and uppermost baffles have ring geometries, the internal diameter of the ring being 1000 mm and the external diameter of the ring extending to the container wall in a sealing manner. Contact tubes are not attached to the baffles in a sealing manner. Instead, gaps of <0.5 mm are left, so that the transverse flow rate of the salt melt was highly constant within a zone.

The central baffle is circular and extends to the outermost contact tubes of the tube bundle.

The circulation of the salt melt is accomplished by two salt pumps, each of which supplies one longitudinal half of the tube bundle.

The pumps force the salt melt into a lower ring channel around the reactor shell, and this channel distributes the salt melt over the periphery of the container. Windows in the reactor shell allows the salt melt in the lowermost longitudinal section to pass into the tube bundle. The salt melt then flows in the sequence, following the baffles, from the outside inward,
from the inside outward,
from the outside inward,
from the inside outward, in an essentially meandrous manner, considered over the container, from bottom to top. Through windows in the uppermost longitudinal section around the container periphery, the salt melt collects in an upper ring channel installed around the reactor shell and, after cooling to the original entry temperature, is pumped back into the lower ring channel.

Contact tube charge, structure of the charge, composition of the reaction mixture and predetermined conversion data: as for A I.

Flow rate of the reaction-gas mixture: 66,530 m$^3$(s.t.p.)/h.

II. Results

The predetermined reaction data (conversion, selectivity, space-time yield) are achieved under the following conditions:

| Conditions | Entry temperature of the salt melt | Exit temperature of the salt melt | Hot-spot temperature | Pump capacity (m$^3$/h) | Flow of salt melt relative to the reaction mixture |
|---|---|---|---|---|---|
| a) | 337° C., Δ = 2° C., | 339° C. | 419° C. | 6,200 | Countercurrent |
| b) | 337° C., Δ = 2° C., | 339° C. | 410° C. | 6,200 | Cocurrent |
| c) | 336° C., Δ = 3° C., | 339° C. | 409° C. | 4,100 | Cocurrent |
| d) | 335° C., Δ = 5° C., | 340° C. | 409° C. | 2,300 | Cocurrent |
| e) | 334° C., Δ = 8° C., | 342° C. | 408° C. | 1,500 | Cocurrent |
| f) | 333° C., Δ = 12° C., | 345° C. | 409° C. | 1,000 | Cocurrent |
| g) | 331° C., Δ = 15° C., | 346° C. | 410° C. | 800 | Cocurrent |

The hot-spot temperature is determined on 5 contact tubes selected radially in the tube bundle equidistantly from the outermost to the innermost. The temperatures given shows the maximum hot-spot value.

Countercurrent flow, considered over the reactor, of salt melt and reaction-gas mixture again clearly shows the worst hot-spot temperatures.

Surprisingly, however, the hot-spot behavior passes through a minimum here, in contrast to A), with decreasing pump capacity (increasing difference between entry and exit temperatures of the heat-exchange medium). With decreasing pump capacity, the inhomogeneities in the temperature profile of the reactor (horizontal section) increase, however, which is why, for stability reasons, a Δ of from 3° to 6° C. between the entry and exit temperatures of the heat-exchange medium is preferred.

This surprising finding is clearly attributable to the fact that the improved heat exchange caused by the transverse flow component and the increased cooling effect due to the reduced entry temperature of the heat-exchange medium for propene conversions of less than 50 mol % improve the hot-spot behavior and the decrease in the space-time yield of acrolein which is associated therewith in this section can, surprisingly, be compensated again by the temperature increase, caused by the heat of reaction, at propene conversions above 50 mol %. One cause of this result may well be that the heat-transfer coefficient on the heat-transfer side of the reaction tubes surprisingly clearly does not decrease to the same extent as the decrease in pump capacity.

A further improvement is therefore possible by removing a part-amount, preferably from 30 to 70 mol % of the feed amount, of the heat-exchange medium at a propene conversion of from 20 to 50 mol %. This causes even better relative cooling and homogenization of the temperature over the reactor cross section at relatively low conversions and at the same time a greater relative temperature increase at high conversions.

At a salt melt feed temperature of 335° C. and a reduction in the circulated amount of salt melt from 5,400 m$^3$/h to 2,700 m$^3$/h (part-amount removed=50%) at the first baffle (flow-control valve) (propene conversion=about 30 mol %), a hot-spot temperature of 404° C. with an exit temperature of 340° C. results under otherwise identical conditions, as stated under B. At the same time, a procedure of this type improves the homogeneity of the temperature profile of the reactor (horizontal section) and the homogeneity of the positions of the hot spots in the individual contact tubes. Decreasing the pump capacity results in considerable costs reduction.

Furthermore, the result in accordance with the invention allows the option either of achieving a longer service life of the catalyst charge at a given space-time yield due to the better hot-spot situation or achieving an increased space-time yield for a given service life by increasing the flow rate.

We claim:

1. A process for the catalytic gas-phase oxidation of propene to acrolein, comprising:

passing a reactant gas mixture comprising propene and oxygen through a plurality of catalyst containing contact tubes in a fixed bed reactor and simultaneously passing only one heat-exchange medium at elevated temperature over the exterior surfaces of the contact tubes in a longitudinal flow pattern which is cocurrent with the direction of flow of the reactants through said tubes;

simultaneously superposing a transverse flow on said longitudinal flow of heat exchange medium by means of an arrangement of successive baffles along the contact tubes which leave passage cross-sections free, thereby resulting in a meandrous flow of the heat-exchange medium through the reactor and setting the flow rate of said heat-exchange medium so that its temperature between the point of entry of the medium into the reactor and its point of exit increases by 2° to 10° C.; and obtaining product acrolein at a selectivity $\geq 85$ mol % from the reactor at a single pass propene conversion $\geq 90$ mol %.

2. The process of claim 1, wherein the temperature of the heat-exchange medium increases by 3° to 6° C. between the point of entry of the medium into the reactor and the point of its exit from the reactor.

3. The process of claim 1 or 2, wherein said arrangement of baffles leaves a passage cross-section free alternately in the center and its outer periphery by successive baffles.

4. The process of claim 1, wherein said tubes are arranged in bundles in an essentially annular manner leaving a free space within the center of the reactor.

5. The process of claim 4, wherein the diameter of the free space in the center of the reactor is about 10 to 30% of the reactor internal diameter.

6. The process of claim 1, wherein the relative diameters of the contact tubes and holes in the baffles through which the contact tubes are positioned are such that gaps exist between the baffle surfaces and the outer surfaces of the contact tubes.

7. The process of claim 6, wherein the widths of the gaps are set so that the transverse flowrate of heat-exchange medium within a zone located between two successive baffles is very constant.

8. The process of claim 1, wherein the baffles are positioned in a non-equidistant arrangement in order to limit temperature differences and pressure drops in a horizontal section within a zone.

9. The process of claim 1, wherein the entry and exit of the heat-exchange medium into the reactor takes place via ring pipelines which are attached to the two ends of the reactor container and have windows distributed over the entire periphery thereof, the window openings being designed in such a way that the same amount of heat-exchange medium passes through each window per time unit.

10. The process of claim 1, wherein a portion of the heat exchange medium is removed from the reactor at a propene conversion ranging from 20 to 50 mol %.

11. The process of claim 10, wherein the range of propene conversion is from 20 to 40 mol %.

12. The process of claim 10, or 11, wherein the portion of heat-exchange medium removed is from 30 to 70% of the total amount of heat-exchange medium fed into the reactor.

13. The process of claim 1, wherein the reactant gas mixture is warmed to the entry temperature of the heat-exchange medium prior to being fed to the catalyst charge.

14. The process of claim 1, wherein the catalyst charge to the contact tubes is a multimetal oxide catalyst comprising molybdenum, bismuth and iron in the form of oxides.

15. The process of claim 1, wherein the heat-exchange medium is a salt melt consisting of 60% by weight of potassium nitrate and 40% by weight of sodium nitrite.

16. A process for the catalytic gas phase oxidation of propene to acrolein, comprising:

passing a reactant gas mixture comprising propene and oxygen, preheated to the temperature of heat-exchange medium in a fixed bed reactor, through a plurality of catalyst containing contact tubes in said fixed bed reactor arranged to leave an essentially circular free space in the center of the reactor of about 10 to 30 vol. % of the reactor internal diameter and containing an arrangement of horizontally positioned baffles, non-equidistantly spaced apart in order to restrict temperature differences and pressure drops in horizontal sections within zones of the reactor, which baffles are positioned to leave alternate heat-exchange medium flow passageways at the center and outer periphery of the reactor, said contact tubes extending through holes in the baffles where the size of the holes is such to accommodate passage of the contact tubes through the baffles and leaving gaps between the outer surfaces of the tubes and the baffles such that the heat-exchange medium passes at a transverse flow rate within a zone between baffles at a constant rate;

simultaneously passing a heat-exchange medium at elevated temperature over the exterior surfaces of the contact tubes in a longitudinal flow pattern which is cocurrent with the direction of flow of reactants through said tubes and superposing a transverse flow on the longitudinal flow of heat exchange medium through the reactor, wherein heat-exchange medium enters a reactor through two ring-shaped pipelines which are attached to the two ends of the reactor and have windows distributed over the entire periphery thereof, the window openings being designed in such a way that the same amount of heat-exchange medium passes through each window per time unit and wherein heat-exchange medium is withdrawn from the reactor as the gas phase oxidation reaction proceeds in an amount of 30 to 70% of the total amount of heat-exchange medium fed into the reactor, the flow rate of heat exchange medium being such that the temperature between the point of entry of the heat exchange medium into the reactor and its point of exit increases by 2° to 10° C.; and obtaining product acrolein at a selectivity $\geq 85$ mol % from the reactor at a single pass propene conversion $\geq 90$ mol %.

* * * * *